United States Patent [19]

Ding et al.

[11] Patent Number: 4,696,527
[45] Date of Patent: Sep. 29, 1987

[54] CABLE CONNECTOR

[75] Inventors: Wolfgang Ding, Brunswick; Werner Arnold, Juechen, both of Fed. Rep. of Germany

[73] Assignee: ARBO Medizin-Technologie GmbH., Braunschweig, Fed. Rep. of Germany

[21] Appl. No.: 864,136

[22] Filed: May 16, 1986

[30] Foreign Application Priority Data

Nov. 25, 1985 [DE] Fed. Rep. of Germany ... 8533107[U]

[51] Int. Cl.$^4$ ...................... H01R 13/66; H01R 29/00
[52] U.S. Cl. ...................................... 439/53; 338/220; 439/502; 439/620; 439/638
[58] Field of Search ......... 339/108 TP, 149 P, 154 A, 339/156 R, 147 R, 150 B, 150 C, 150 T, 151 B, 151 C, 18 R, 18 B, 18 C, 18 P, 28; 338/220

[56] References Cited

U.S. PATENT DOCUMENTS

| | | | |
|---|---|---|---|
| 1,706,158 | 3/1929 | Hendricks, Jr. | 339/108 TP |
| 2,417,369 | 3/1947 | Luhn | 339/18 B |
| 2,733,418 | 1/1956 | Kimble | 339/108 TP |
| 2,885,648 | 5/1959 | King | 339/108 TP |
| 2,960,673 | 11/1960 | Young | 338/220 |
| 3,646,579 | 2/1972 | DiVita et al. | 339/108 TP |
| 3,990,763 | 11/1976 | Kress | 339/156 R |
| 4,205,386 | 5/1980 | Ruszala et al. | 338/220 |
| 4,585,290 | 4/1986 | Knickerbocker et al. | 339/156 R |

Primary Examiner—Gil Weidenfeld
Assistant Examiner—Gary F. Paumen
Attorney, Agent, or Firm—Schwartz, Jeffery, Schwaab, Mack, Blumenthal & Evans

[57] ABSTRACT

A cable connector for a multiplicity of electrical lines is disclosed. The cable connector is adapted to be connected to a banana plug. A protective resistor is provided inside the cable connector in order to protect the electrical lines. By providing the protective resistor inside of the cable connector, a banana plug insulating jacket can be more easily provided in the banana plug housing, and the cable connector remains protected at all times.

3 Claims, 3 Drawing Figures

CABLE CONNECTOR

FIELD OF THE INVENTION

The invention relates to a cable connector for a multiplicity of measuring electrodes extending from a living body to an evaluation device. Specifically, the evaluation device has a plurality of single lines plugged into a plug and socket connector, the lines being protected by a protective resistor.

RELATED ART

Such cable connectors are known. The single lines are, in these cases, generally connected to the measuring electrodes by banana plugs. The other ends have in each case a plug which can be plugged into an n-pole lying plug and socket connector, n being the number of single lines. The known plug and socket connector is firmly joined to a trunk cable, to which an appliance inlet is welded at its other end.

As such arrangements are also used for defibrillation, in which electric shocks are imparted to the body via electrodes, the single lines must have protective resistors. In the known cable connector arrangement, these are accommodated in the banana plugs. If emergency repairs are necessary on the cable connector, it may happen that the banana plug is bridged, so that the necessary protective resistance is not effective. Furthermore, the known cable connector has the disadvantage that damage to the trunk cable requires a very expensive replacement, as the trunk cable has to be exchanged with the plug and socket connector and the appliance inlet.

SUMMARY OF THE INVENTION

The invention is based on the object of providing a cable connector for a plurality of measuring electrodes wherein a high flexibility in use and safety from overcurrents are better ensured.

This object is achieved according to the invention by the protective resistors in the plug and socket connector being arranged behind the socket-contacts for the single lines and the plug and socket connector having a multipole plug and socket connection corresponding to the number of single lines.

In the case of the cable connector according to the invention, the protective resistors are accommodated in the plug and socket connector, which is designed as a separate part and into which both the single lines and also, if necessary, the trunk cable can be plugged. In cases of special application, the plug and socket connector may also be plugged directly into an evaluation device, so that the trunk cable is completely superfluous.

The arrangement of the protective resistors in the plug and socket connector has the advantage that the resistors remain effective in any case—irrespective of the type of single lines used. Furthermore, it is then possible to design the banana plugs as protective plugs by surrounding them circumferentially with an insulating jacket which can be pushed into the banana plug housing against a restoring spring. In this case, the tip of the banana plugs is provided with an insulating terminating piece. The banana plugs not plugged into the electrodes are therefore shockproof unless the jacket is pushed back against the restoring spring.

As the plug and socket connector is a separate part, the trunk cable which may be required can be exchanged at relatively low cost in the event of damage, as the plug and socket connector is not affected by this.

The above and other objects are achieved by a cable connector comprising a housing means having electrically connected input and output terminals and a protective resistor connected in parallel with the electrical connection between input and output terminals.

BRIEF DESCRIPTION OF THE DRAWINGS

The invention is to be explained in more detail below with reference to an exemplary embodiment illustrated in the drawings, in which.

DETAILED DESCRIPTION OF THE PREFERRED EMBODIMENT

Figure 1:
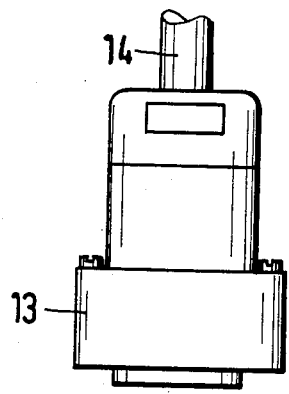
FIG. 1 shows a side view of a cable connector according to one embodiment of the invention.
Figure 2:
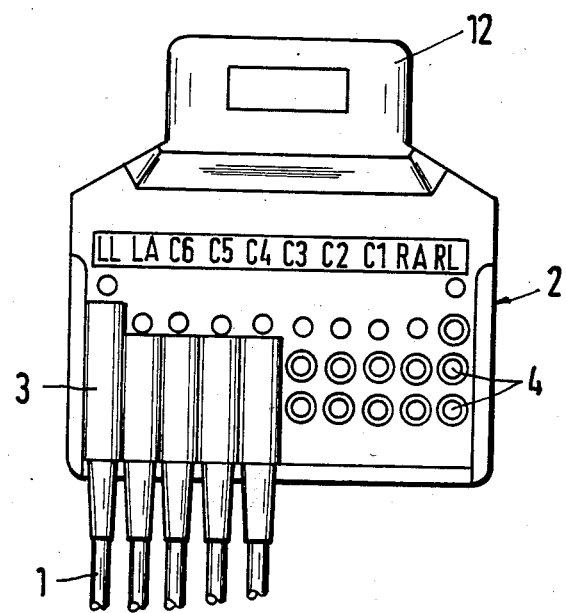
FIG. 2 shows a plan view of the plug-in side of the cable connector.
Figure 2:
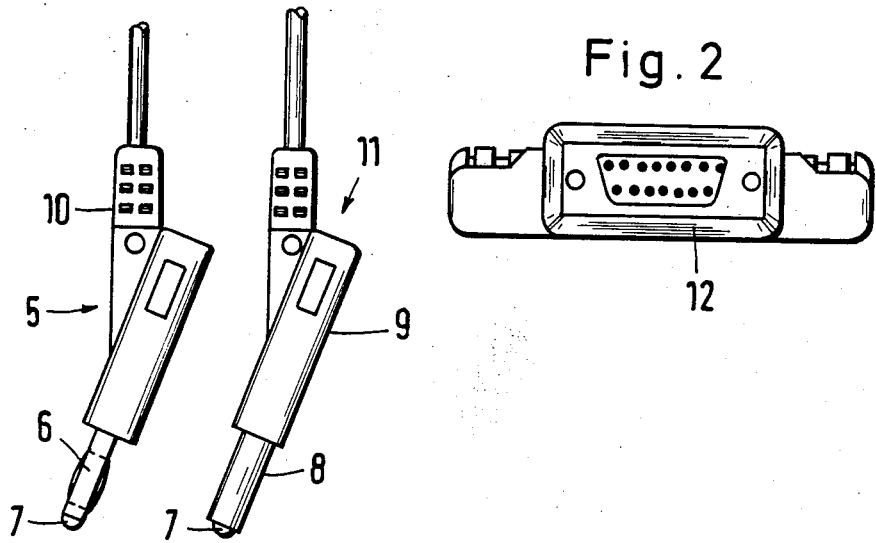

FIG. 1 shows a multiplicity of single lines 1. Ten single lines 1 can be plugged into a plug and socket connector 2 with the aid of two-pole of multipole plugs 3, the poles of which are generally perpendicular to the axis of the single cable 1, into corresponding sockets 4 of the plug and socket connector 2. The other ends of the single lines 1 are provided with safety banana plugs 5, of which only two are illustrated in FIG. 1. The banana plugs 5 have a conventional banana plug contact 6, and an insulating terminating piece 7 provided at the tip of banana plug contact 6. In the non plugged-in state, the plug contact 6 is covered by a jacket 8 of insulating material, for example plastic. The jacket 8 can be pushed against the force of a restoring spring into the housing 9 of the banana plug 5. The banana plug 5 illustrated on the left in FIG. 1 shows the plug contact 6 after the jacket 8 has been pushed into the housing 9. The housing 9 is at an acute angle to the connecting piece 10 of the single cable 1 and is provided at its rear end with a socket 11, into which a banana plug contact 6 can be pushed for test purposes.

The plug and socket connector 2 is designed as a separate part and has sockets 4 arranged in a panel shape on a first flat side. The housing of the plug and socket connector 2 is tapered rearwardly and has a plug and socket connection 12. The number of contacts provided on plug and socket connection 12 depends on the number of single lines 1. A plug 13 of a trunk cable 14 can be pushed into the plug and socket connection. The plug 13 is ten-wired in the exemplary embodiment illustrated. However, it is also possible to plug the plug and socket connection 12 onto a corresponding plug of an evaluation device.

Figure 3:
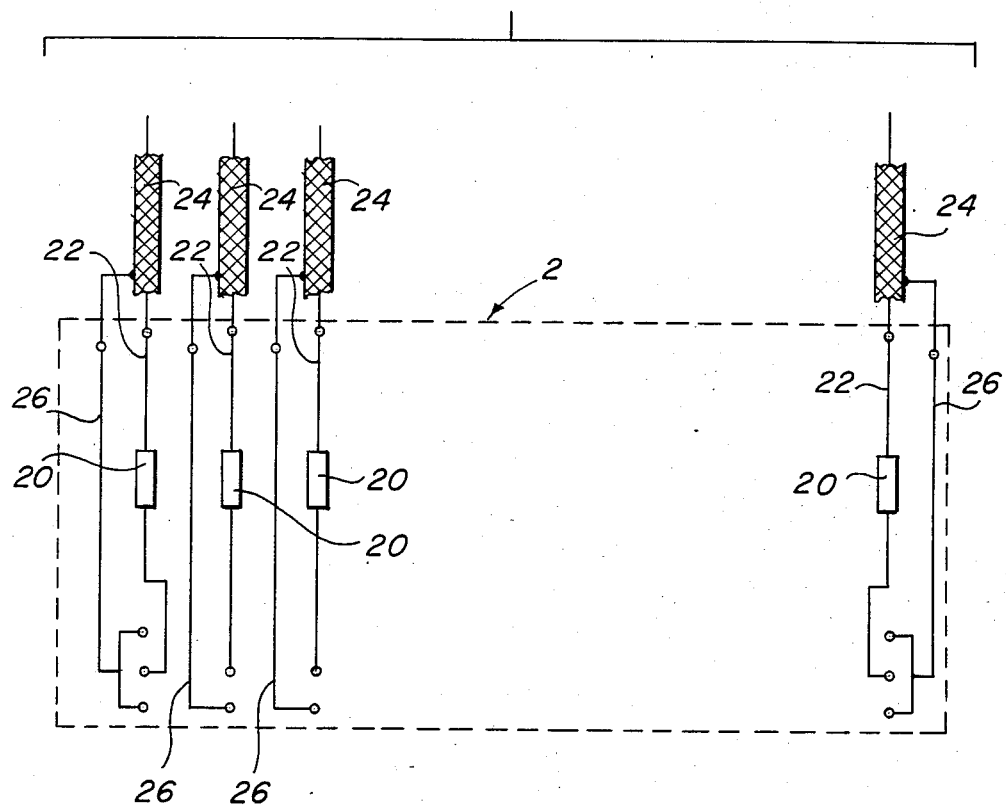
FIG. 3 shows the electrical connection of a protective resistor in the embodiment of FIG. 1.

The plug and socket connector 2 has protective resistors 20 connected in series with the signal lines 22 in order to limit current through the signal lines, as shown in FIG. 3. The signal lines 22 are shielded in cable 14 with screening 24. The shielding to each signal line 22 is connected to a lead 26 attached to a contact of socket 4. By disposing resistors 20 in connector 2, it is no longer necessary to provide a separate protective resistor in each banana plug 5. Accordingly, more free space is available in banana plug 5 for accommodating the jacket 8. This space was not available in the housing 9 when the housing 9 had to encompass the protective resistor.

For a number of plugs 3 which can be plugged in at the edge, the plug and socket connector 2 has numerous sockets 4 which are connected such that the associated plugs 3 (LL and RL) can also be plugged in a position turned through 180°. This permits special electrodes (for example for attaching to the legs) to be connected in certain circumstances without any major kinks in the cable.

While one embodiment of the invention has been described, it will be understood that is capable of further modification, and this application is intended to cover any variations, uses, or adaptions of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A cable connector arrangement which connects a multiplicity n of separate body electrode cables to an at least n-pole trunk cable having a first connector fixedly connected thereto that is connectable to a control apparatus, comprising:
    an intermediate connector having a plurality of contacts which receives one end of the body electrode cables and having a second connector for receiving the first connector of said trunk cable; and
    protective resistors within the intermediate connector, each arranged in series in an electrical connection with at least one of said contacts and a pole of said second connector.

2. The cable connector according to claim 1, wherein the other end of each body electrode cable is connected to a banana plug, said banana plug comprising:
    an electrically conductive connector contact having a non-conductive insulating tip;
    an insulating jacket slidably disposed around said connector contact; and
    a housing means adapted to receive said insulating jacket having a restoring spring means for normally biasing said insulating jacket in a position surrounding said connector contact.

3. The cable connector according to claim 1, wherein the other ends of the multiplicity of body electrode cables are connected to;
    a plurality of banana plugs each of said banana plugs comprising:
        an electrically conductive connector contact having a non-conductive insulating tip;
        an insulating jacket slidably disposed around said connector contact; and
        a housing means adapted to receive said insulating jacket having a restoring spring means for normally biasing said insulating jacket in a position surrounding said connector contact.

* * * * *